United States Patent
Georgiadis et al.

(10) Patent No.: US 7,297,932 B2
(45) Date of Patent: Nov. 20, 2007

(54) VEHICLE OPTOELECTRONIC PRECIPITATION SENSOR WITH ADJUSTABLE LENS HOLDER

(75) Inventors: Christos Georgiadis, Dortmund (DE); Michael Röhr, Dortmund (DE); Frank Hagen, Lüdenscheid (DE); Thomas Weber, Lüdenscheid (DE); Matthias Richwin, Dortmund (DE)

(73) Assignee: Leopold Kostal GmbH & Co. KG, Ludenscheid (DE)

(*) Notice: Subject to any disclaimer, the term of this patent is extended or adjusted under 35 U.S.C. 154(b) by 13 days.

(21) Appl. No.: 11/398,105

(22) Filed: Apr. 5, 2006

(65) Prior Publication Data

US 2006/0237635 A1 Oct. 26, 2006

(30) Foreign Application Priority Data

Apr. 21, 2005 (DE) .................. 10 2005 018 379

(51) Int. Cl.
*G01F 23/00* (2006.01)
(52) U.S. Cl. ............... 250/227.25; 250/573; 250/574; 257/80; 257/81; 340/602; 73/29.01; 73/29.05
(58) Field of Classification Search ........ 250/573–575, 250/227.25, 239; 340/600, 602, 603; 318/483, 318/643; 73/29.01, 335.01, 29.02, 29.05; 257/80, 81, 84, 431–434, 678, 680
See application file for complete search history.

(56) References Cited

U.S. PATENT DOCUMENTS 5,572,017 A * 11/1996 Veltum et al. ......... 250/227.25
5,639,393 A * 6/1997 Veltum et al. ............. 219/209
6,285,037 B1 * 9/2001 Koyama et al. ........... 250/574
6,995,354 B2 2/2006 Hagen et al.
2005/0092901 A1 5/2005 Hagen et al.

FOREIGN PATENT DOCUMENTS

| DE | 43 29 608 C1 | 1/1995 |
| DE | 101 04 653 A1 | 8/2002 |
| DE | 101 56 241 A1 | 6/2003 |
| DE | 102 24 692 A1 | 1/2004 |

* cited by examiner

*Primary Examiner*—Davienne Monbleau
(74) *Attorney, Agent, or Firm*—Brooks Kushman P.C.

(57) ABSTRACT

An optoelectronic sensor for sensing wetting of a windshield includes a first circuit, and a radiation emitter and a radiation detector both arranged on the first circuit to emit radiation toward the windshield and to detect radiation reflected from the windshield. Beam shapers parallelize the emitted radiation toward the windshield and focus radiation reflected from the windshield toward the detector. A coupling element couples the emitted radiation into the windshield and couples the reflected radiation out of the windshield. A structural element is arranged between the lens holder and the coupling element. The structural element may have retaining elements for positioning a second circuit arranged between the lens holder and the structural element relative to the windshield. The structural element may have support elements for adjustably positioning the lens holder and thereby the beam shapers relative to the first circuit and the windshield.

17 Claims, 1 Drawing Sheet

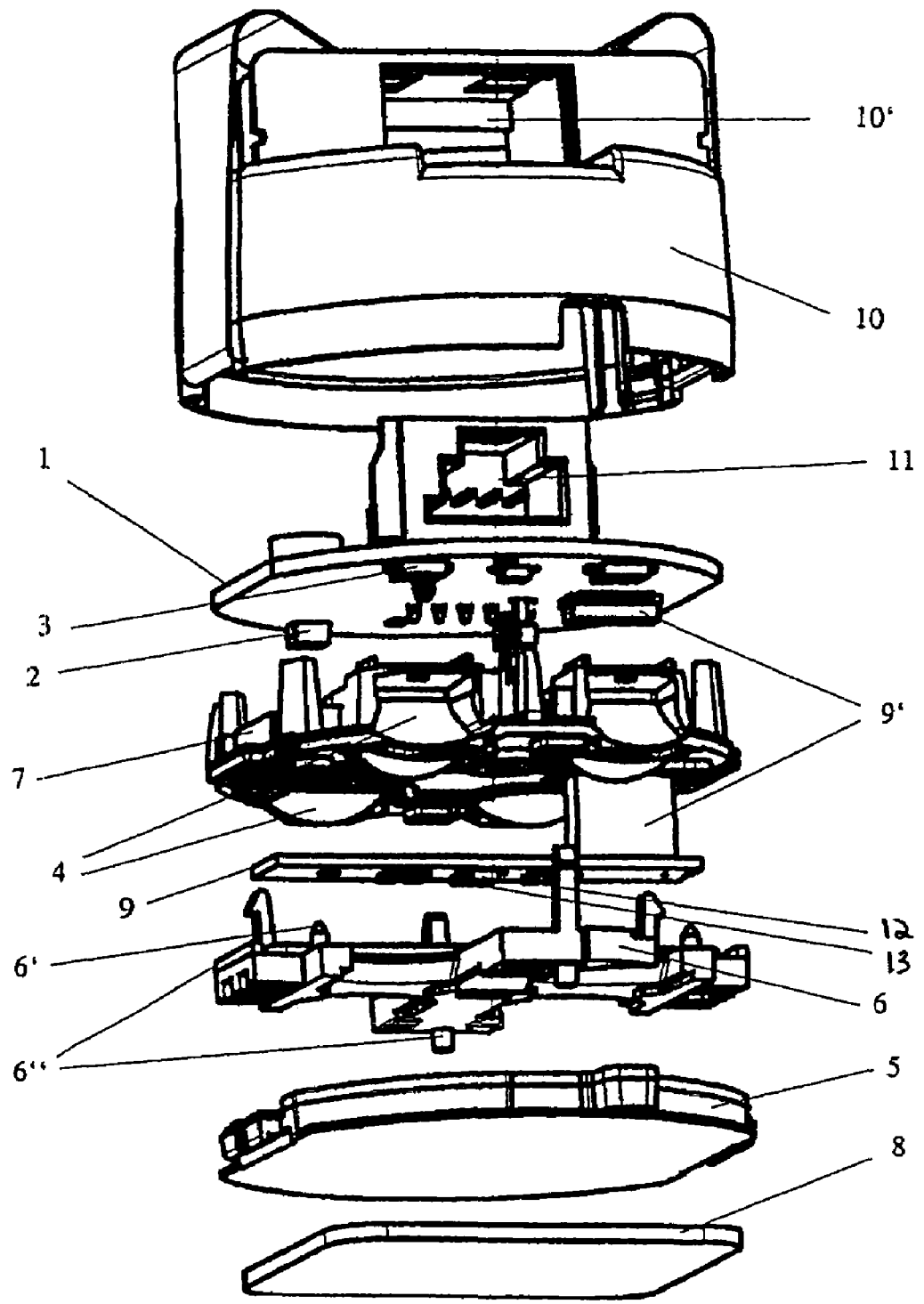

VEHICLE OPTOELECTRONIC PRECIPITATION SENSOR WITH ADJUSTABLE LENS HOLDER

CROSS-REFERENCE TO RELATED APPLICATIONS

This application claims priority to DE 10 2005 018 379.4, filed Apr. 21, 2005, which is hereby incorporated by reference.

BACKGROUND OF THE INVENTION

1. Field of the Invention

The present invention relates to an optoelectronic sensor device for sensing the wetting of a transparent motor vehicle windshield having precipitation in which the sensor device includes a radiation emitter and a radiation detector arranged on a first circuit support, beam shaping means for parallelizing and directing optical radiation emitted by the emitter toward the windshield and for focusing and directing the radiation toward the detector after the radiation has reflected off the windshield, and a coupling element for coupling the radiation into and out of the windshield.

2. Background Art

DE 101 04 653 A1 discloses an optoelectronic sensor device of this type. The sensor device includes a radiation conductor and a coupling element. The radiation conductor has a radiation exit surface and a radiation entrance surface. The coupling element is attached to the inside surface of a windshield. The coupling element has profiles which have radiation in-coupling areas on first sides and radiation out-coupling areas on second sides. The radiation in-coupling areas are oriented parallel to the radiation exit surface of the radiation conductor. The radiation out-coupling areas are oriented parallel to the radiation entrance surface of the radiation conductor. The profiles make it possible to do without direct coupling of the radiation conductor to the inside windshield surface.

In order to allow optimal use of the radiation beam cross-section with several different windshield thicknesses, and to do so without changing the structure of the radiation conductor, the sensor device includes means for adjusting the position of the radiation conductor relative to the windshield. As such, the position adjusting means adjust the distance of the radiation entrance and exit surfaces of the radiation conductor relative to the inside windshield surface. In this sensor device, the position adjusting means are on the radiation conductor itself and/or on a base which holds the radiation conductor in position relative to the windshield.

SUMMARY OF THE INVENTION

Compared with the sensor device of the background art, an optoelectronic sensor device for sensing wetting of a motor vehicle windshield having precipitation in accordance with the present invention realizes greater functionality while having a structure that is more compact and more robust against interference.

In one embodiment, the sensor device in accordance with the present invention includes a first circuit support, a radiation emitter arranged on the first circuit support to emit radiation toward a windshield, and a radiation detector arranged on the first circuit support to detect radiation reflected back from the windshield. The sensor device further includes a lens holder which holds beam shaping means respectively associated with the emitter and the detector. The beam shaping means associated with the emitter parallelizes and directs the radiation emitted by the emitter toward the windshield and the beam shaping means associated with the detector focuses and directs radiation reflected back from the windshield toward the detector. The sensor device further includes a coupling element optically associable with the windshield for coupling the radiation emitted by the emitter into the windshield and for coupling the radiation reflected back from the windshield out of the windshield. The sensor device further includes a structural element arranged between the lens holder and the coupling element and further includes a second circuit support arranged between the lens holder and the structural element. The structural element has retaining elements for holding and positioning the second circuit support relative to the windshield.

In this embodiment, the structural element may further include means for adjustably positioning the lens holder such that the distances between the beam shaping means relative to the emitter and the detector and the windshield are adjustable. The means for adjustably positioning the lens holder include rest and/or support elements of the structural element.

In another embodiment, the sensor device in accordance with the present invention includes the first circuit support, the radiation emitter, the radiation detector, the lens holder which holds the beam shaping means respectively associated with the emitter and the detector, the coupling element, and the structural element which again is arranged between the lens holder and the coupling element. In this embodiment, the structural element includes means for adjustably positioning the lens holder such that the distance between the beam shaping means is adjustable relative to the windshield.

The sensor device in accordance with the present invention realizes relatively greater functionality while being relatively more compact and more robust against interference by having a structural element arranged between the first circuit support and the coupling element in which the structural element includes retaining elements which hold and position a circuit support in the vicinity of the windshield.

Advantageously, in an embodiment, the structural element includes, in addition to retaining elements for holding and positioning the second circuit support in the vicinity of the windshield, means for adjusting the position and distance of beam shaping means arranged on the lens holder relative to the windshield. This gives the sensor device an especially compact structure.

Preferably, the means for adjusting the distance of the beam shaping means relative to the windshield are rest and/or support elements which are made as a unitary piece with the structural element and which are associated on a top side of the structural element with the lens holder (which holds the beam shaping means) and associated on a bottom side of the structural element with the coupling element.

In an embodiment, the structural element acts as a cover overlapping on its top side at least part of the second circuit support in order to protect the second circuit support from electrostatic discharge (ESD) and improperly applied forces and to improve the electromagnetic compatibility of the second circuit portion. The structural element includes metal or a metallic or conductive coating on at least the portion of the structural element which acts as the cover overlapping the second circuit support in order to provide the noted benefits.

In an embodiment, other radiation detectors are integrated with the sensor device. These other radiation detectors may be employed to sense light conditions outside of the motor vehicle, sense solar radiation penetrating into the motor vehicle, etc. Some of these other radiation detectors may also be arranged on the first circuit support. In this case, these other radiation detectors can be associated with other beam shaping means held by the lens holder. In an embodiment, at least one other radiation detector is arranged on the second circuit support, which is arranged within the sensor device between the first circuit support and the structural element in the vicinity of the windshield.

The structural element can fulfill other functions in embodiments of the sensor device having additional radiation detectors. For example, the structural element can have refractive or diffractive structures approximately in areas where the structural element overlaps the additional radiation detectors; the structural element can have diaphragm structures affecting the positional and angular dependence or the spectral composition of radiation; the structural element can have optical filters; etc.

The optical effect of the beam shaping means may be supplemented or expanded in order, for example, to implement different variants of the sensor device by making the structural element in the form of a cover overlapping at least parts of the beam shaping means and by providing the structural element with refractive or diffractive structures. Diaphragm structures and/or optical filters in the portion of the structural element acting as the cover overlapping the beam shaping means may be employed to affect the positional and angular dependence or spectral composition of the radiation.

The above features, other features, and advantages of the present invention are readily apparent from the following detailed description thereof when taken in connection with the accompanying drawing.

BRIEF DESCRIPTION OF THE DRAWINGS

The FIGURE illustrates an exploded view of an optoelectronic sensor device in accordance with an embodiment of the present invention.

DETAILED DESCRIPTION OF THE PREFERRED EMBODIMENT(S)

Referring now to the FIGURE, an optoelectronic sensor device in accordance with an embodiment of the present invention is shown. The sensor device includes a first circuit support 1 in the form of an electrical circuit board. A radiation emitter(s) 2 and a radiation detector(s) 3 are arranged on a bottom side of first circuit support 1. Radiation emitter 2 and radiation detector 3 are preferably surface mounted devices (SMD). A lens holder 7 is directly associated with the bottom side of first circuit support 1. Lens holder 7 holds beam shaping means 4. Beam shaping means 4 are respectively associated with each radiation emitter 2 and radiation detector 3. A coupling element 5 having a profile(s) is optically conductively coupled by an optically transparent adhesive layer 8 to the inside windshield surface.

In general, beam shaping means 4 associated with radiation emitter 2 parallelizes optical radiation emitted from radiation emitter 2 and directs the radiation toward the windshield. The radiation enters the windshield from the inside windshield surface and then is reflected back by the outside windshield surface. Beam shaping means 4 associated with radiation detector 3 focuses and directs the reflected radiation toward radiation detector 3.

More particularly, radiation emitter 2 emits optical radiation toward beam shaping means 4 associated with radiation emitter 2. Beam shaping means 4 associated with radiation emitter 2 parallelizes the radiation as a beam and directs the radiation beam towards radiation in-coupling areas of coupling element 5. The radiation beam passes through the radiation in-coupling areas of coupling element 5, enters the windshield from the inside windshield surface, and passes through the windshield to the outside windshield surface. The radiation beam reflects off the outside windshield surface back through the windshield toward the inside windshield surface. The reflected radiation passes out through the inside windshield surface and through radiation out-coupling areas of coupling element 5 toward beam shaping means 4 associated with radiation detector 3. Beam shaping means 4 associated with radiation detector 3 focuses and directs the reflected radiation as a beam toward radiation detector 3 which then receives the reflected radiation beam.

The sensor device requires a proper radiation beam geometry in order to function properly given a specified windshield thickness. The proper radiation beam geometry for a given specified windshield thickness is achieved when the distances between the windshield, beam shaping means 4, and radiation emitter 2 and radiation detector 3 are set appropriately.

In accordance with the present invention, the sensor device includes a structural element 6 which is used to realize the appropriate distances between beam shaping means 4 and radiation emitter 2 and radiation detector 3 and between beam shaping means 4 and the windshield. Structural element 6 is arranged between lens holder 7 (which holds beam shaping means 4) and coupling element 5. The position of lens holder 7, which is arranged between first circuit support 1 and structural element 6, and thus (a) the position of beam shaping means 4 with respect to radiation emitter 2 and radiation detector 3 and (b) the position of beam shaping means 4 with respect to the windshield, is adjustable by corresponding rest or support elements 6" arranged on structural element 6. Support elements 6" support the top side of structural element 6 against lens holder 7 and support the bottom side of structural element 6 against coupling element 5.

A second circuit support 9, in the form of an electrical circuit board, is arranged between lens holder 7 and structural element 6. Second circuit support 9 holds heating elements 13 for adjusting the temperature of the sensor device and holds other radiation detector(s) 12. Radiation detectors 12 are provided to produce signals to control, for example, vehicle lighting or vehicle air conditioning. Second circuit support 9 is electrically connected with primary circuit support 1 through a plug-and-socket connection 9'.

The top side of structural element 6 includes corresponding retaining elements 6' which hold, fasten, and position second circuit support 9 in a position relatively close to the windshield. As such, the position of second circuit support 9, and thereby, the position of radiation detectors 12, with respect to the windshield is adjustable by the corresponding retaining elements 6' on the top side of structural element 6.

In the line of sight path between the windshield and radiation detectors 12 on second circuit support 9, structural element 6 includes: refractive or diffractive structures to shape the beam of incident radiation with positional or angular dependence; diaphragm structures affecting the spectral composition of the radiation; optical filters; etc.

In addition to the functions mentioned, structural element 6 can also be used, for example, to control the output of a heater arranged on either circuit support 1 or 9 in order to make the heat more homogeneous or to carry fastening forces away from coupling element 5 to other elements of the sensor device. A housing 10 contains the entire sensor device. Housing 10 includes an opening 10' which allows outside access to a plug-and-socket connector 11 on first circuit support 1. Plug-and-socket connector 11 enables the sensor device to be electrically connected to a motor vehicle electrical system.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An optoelectronic sensor device for sensing wetting of a motor vehicle windshield having precipitation, the sensor device comprising:
   a first circuit support;
   a radiation emitter arranged proximate to the first circuit support to emit radiation toward a windshield;
   a radiation detector arranged proximate to the first circuit support to detect radiation reflected back from the windshield;
   a lens holder holding beam shaping means respectively associated with the radiation emitter and the radiation detector, wherein the beam shaping means associated with the radiation emitter parallelizes and directs at least some of radiation emitted by the radiation emitter toward the windshield, wherein the beam shaping means associated with the radiation detector focuses and directs at least some radiation reflected back from the windshield toward the radiation detector;
   a coupling element for coupling at least some radiation emitted by the radiation emitter into the windshield and for coupling at least some radiation reflected back from the windshield out of the windshield;
   a structural element arranged between the lens holder and the coupling element; and
   a second circuit support arranged between the lens holder and the structural element;
   wherein the structural element has retaining elements for holding and positioning the second circuit support relative to the windshield.

2. The sensor device of claim 1 wherein:
   the structural element includes means for positioning the lens holder relative to the windshield.

3. The sensor device of claim 2 wherein:
   the means for positioning the lens holder include support elements of the structural element.

4. The sensor device of claim 1 wherein:
   the structural element overlaps at least part of the second circuit support to protect the second circuit support from electrostatic discharge and improperly applied forces.

5. The sensor device of claim 1 further comprising:
   a plug-and-socket connector which electrically connects the first and second circuit supports.

6. The sensor device of claim 1 further comprising:
   heating elements arranged on the second circuit support.

7. The sensor device of claim 1 further comprising:
   at least one additional radiation detector, wherein the at least one additional radiation detector is arranged on the second circuit support for sensing at least one of light conditions outside the motor vehicle, solar radiation penetrating into the motor vehicle, and condensation present on the inside windshield surface.

8. The sensor device of claim 7 wherein:
   the structural element includes structures having refractive or diffractive properties in an area overlapping the at least one additional radiation detector.

9. The sensor device of claim 7 wherein:
   the structural element includes diaphragm structures in an area overlapping the at least one additional radiation detector, wherein the diaphragm structures affect at least one of positional dependence, angular dependence, spectral composition of the radiation, and optical filtering.

10. The sensor device of claim 1 wherein:
    the structural element overlaps parts of the beam shaping means and includes, in areas overlapping the beam shaping means, refractive or diffractive structures which supplement the radiation parallelizing and focusing of the beam shaping means.

11. The sensor device of claim 1 wherein:
    the structural element overlaps parts of the beam shaping means and includes, in areas overlapping the beam shaping means, diaphragm structures.

12. The sensor device of claim 1 wherein:
    the structural element overlaps parts of the beam shaping means and includes, in areas overlapping the beam shaping means, optical filters.

13. The sensor device of claim 12 wherein:
    the optical filters affect spectral composition of the radiation.

14. An optoelectronic sensor device for sensing wetting of a motor vehicle windshield having precipitation, the sensor device comprising:
    a first circuit support;
    a radiation emitter arranged proximate to the first circuit support to emit radiation toward a windshield;
    a radiation detector arranged proximate to the first circuit support to detect radiation reflected back from the windshield;
    a lens holder holding beam shaping means respectively associated with the radiation emitter and the radiation detector, wherein the beam shaping means associated with the radiation emitter parallelizes and directs at least some radiation emitted by the radiation emitter toward the windshield, wherein the beam shaping means associated with the radiation detector focuses and directs at least some radiation reflected back from the windshield toward the radiation detector;
    a coupling element for coupling at least some radiation emitted by the radiation emitter into the windshield and for coupling at least some radiation reflected back from the windshield out of the windshield;
    a structural element arranged between the lens holder and the coupling element, wherein the structural element includes means for positioning the lens holder relative to the coupling element; and
    a second circuit support arranged between the lens holder and the structural element, wherein the structural element has retaining elements for holding and positioning the second circuit support relative to the coupling element.

15. The sensor device of claim 14 wherein:
    the means for positioning the lens holder include support elements of the structural element.

16. The sensor device of claim 14 wherein:
the structural element overlaps at least part of the second circuit support to protect the second circuit support from electrostatic discharge and improperly applied forces.

17. The sensor device of claim 14 further comprising:
a plug-and-socket connector which electrically connects the first and second circuit supports.

* * * * *